(12) United States Patent
Wang et al.

(10) Patent No.: US 11,634,388 B2
(45) Date of Patent: Apr. 25, 2023

(54) CRYSTAL FORM OF LENVATINIB MESYLATE AND PREPARATION METHOD THEREFOR

(71) Applicant: Chengdu Easton Biopharmaceuticals Co., Ltd., Chengdu (CN)

(72) Inventors: Ying Wang, Chengdu (CN); Xuehai Pang, Chengdu (CN); Haijian Huo, Chengdu (CN); Xiaochao Xian, Chengdu (CN); Huike Gu, Chengdu (CN)

(73) Assignee: Chengdu Easton Biopharmaceuticals Co., Ltd., Chengdu (CN)

( * ) Notice: Subject to any disclaimer, the term of this patent is extended or adjusted under 35 U.S.C. 154(b) by 92 days.

(21) Appl. No.: 17/059,708

(22) PCT Filed: May 31, 2019

(86) PCT No.: PCT/CN2019/089398
§ 371 (c)(1),
(2) Date: Nov. 30, 2020

(87) PCT Pub. No.: WO2019/228485
PCT Pub. Date: Dec. 5, 2019

(65) Prior Publication Data
US 2021/0214309 A1  Jul. 15, 2021

(30) Foreign Application Priority Data

Jun. 1, 2018 (CN) .......................... 201810557062.0

(51) Int. Cl.
*C07D 215/48* (2006.01)
*A61K 31/47* (2006.01)
*A61P 35/00* (2006.01)

(52) U.S. Cl.
CPC ........ *C07D 215/48* (2013.01); *C07B 2200/13* (2013.01)

(58) Field of Classification Search
CPC .. C07D 215/48; C07B 2200/13; A61K 31/47; A61P 35/00
See application file for complete search history.

(56) References Cited

U.S. PATENT DOCUMENTS

2018/0155291 A1  6/2018  Chen

FOREIGN PATENT DOCUMENTS

| AU | 2004-309217 B2 | 11/2008 | |
|---|---|---|---|
| CN | 101337931 A | 1/2009 | |
| CN | 107266363 A | 10/2017 | |
| WO | WO-2005063713 A1 * | 7/2005 | ........... C07D 215/48 |
| WO | WO 2016/184436 A1 | 11/2016 | |

OTHER PUBLICATIONS

International Search Report in International Application No. PCT/CN2019/089398, dated Aug. 29, 2019 (6 pages).

* cited by examiner

*Primary Examiner* — John M Mauro
(74) *Attorney, Agent, or Firm* — Nixon Peabody LLP

(57) ABSTRACT

A new crystal form of lenvatinib mesylate, a preparation method thereof and a use thereof in the preparation of a drug for treating cancer.

6 Claims, 11 Drawing Sheets

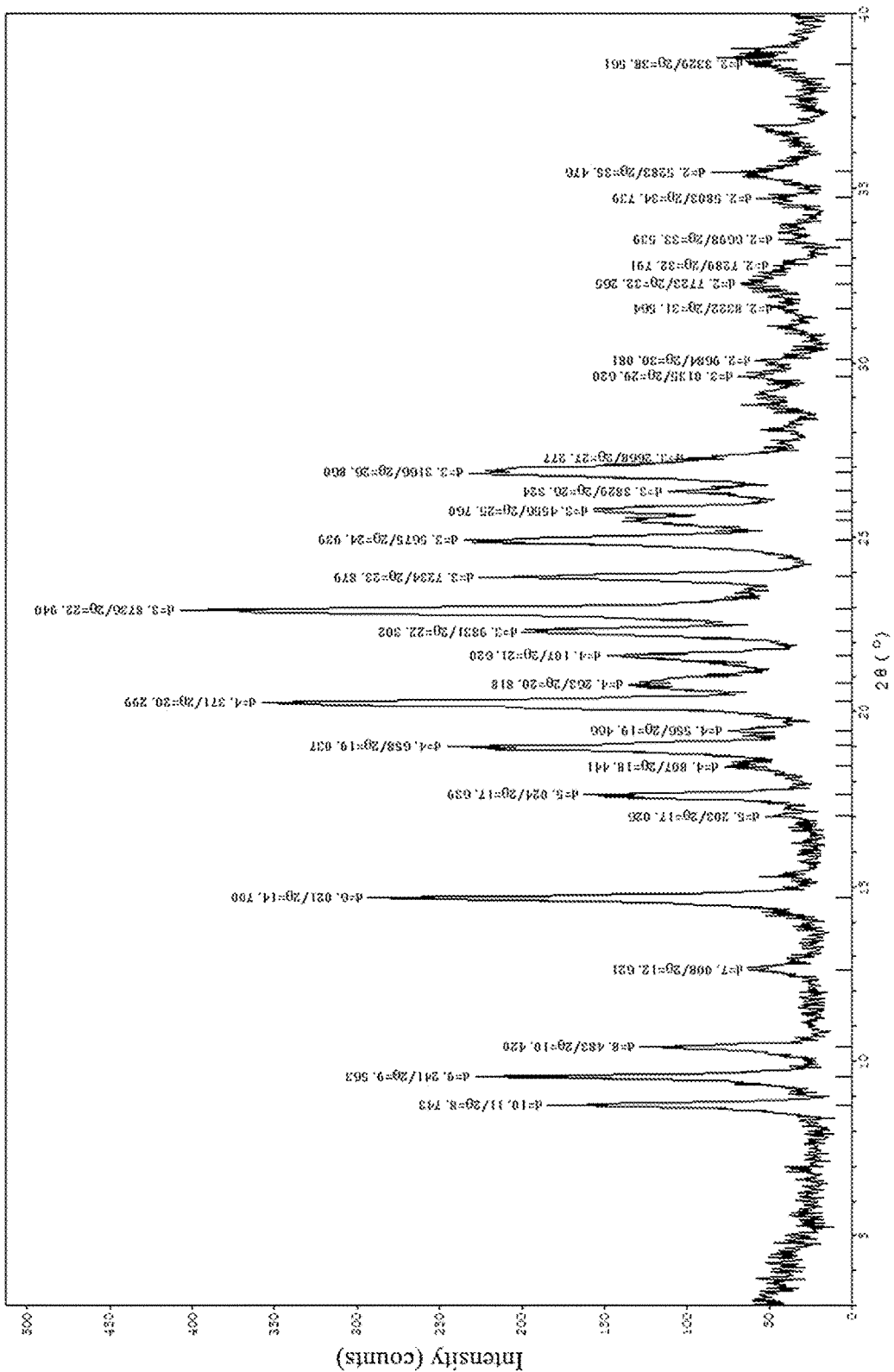
Fig. 7a1

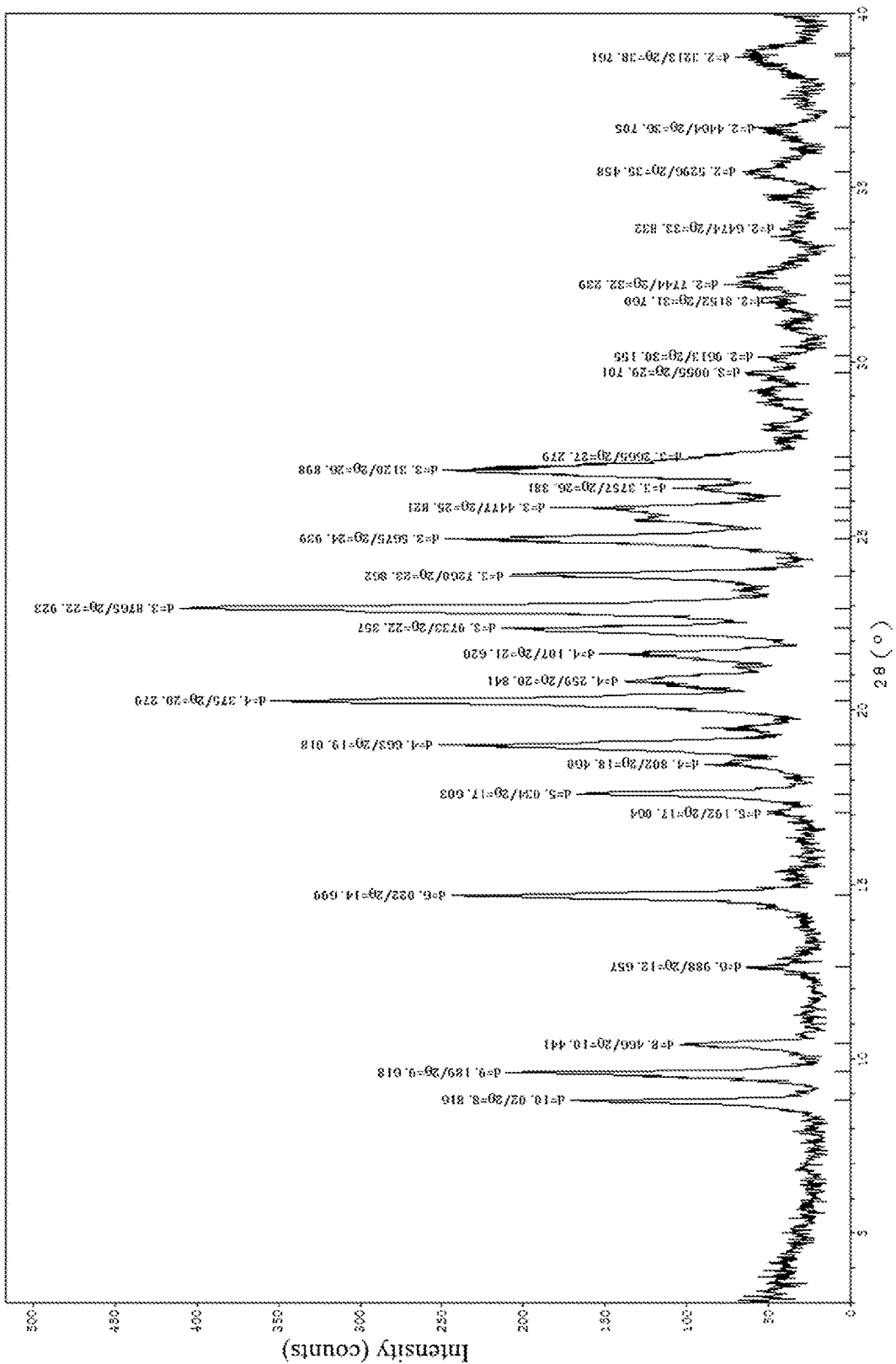
Fig. 7a2

CRYSTAL FORM OF LENVATINIB MESYLATE AND PREPARATION METHOD THEREFOR

REFERENCES TO RELATED APPLICATIONS

This application is a U.S. national stage of PCT/CN2019/089398 filed on May 31, 2019, which claims the benefit of Chinese patent application No. 201810557062.0, filed on Jun. 1, 2018, the contents of which are all incorporated herein by reference in their entireties.

FIELD OF THE INVENTION

The invention relates to the field of pharmaceutical crystal forms, in particular to a new crystal form of lenvatinib mesylate as well as preparation method and use thereof.

BACKGROUND OF THE INVENTION

Lenvatinib, the chemical name of which is 4-[3-chloro-4-(cyclopropylaminocarbonyl)aminophenoxy]-7-methoxy-6-quinolinecarboxamide, has a structural formula represented by formula (I),

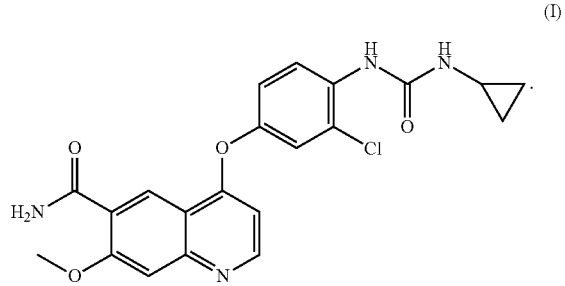 [SMILES: COc1cc2nccc(Oc3ccc(NC(=O)NC4CC4)c(Cl)c3)c2cc1C(N)=O]

Lenvatinib is a medicament for thyroid carcinoma developed by Japan Eisai Co., Ltd. Lenvatinib is an oral multi-receptor tyrosine kinase (RTK) inhibitor with a novel binding mode to its receptors. In addition to inhibiting other pro-angiogenic and carcinogenic signaling pathway related RTKs involved in tumor proliferation, it can selectively inhibit the kinase activity of vascular endothelial growth factor (VEGF) receptor. It was approved by the FDA on Feb. 13, 2015 for the treatment of patients with locally recurrent or metastatic, progressive, radioactive iodine-refractory differentiated thyroid cancer. It was subsequently approved for marketing in European Union and Japan.

Lenvatinib mesylate is non-hygroscopic, not a solvate, but polymorphic. Crystal forms A, B, C, F (hydrate) and I (acetic acid solvate) of lenvatinib mesylate are disclosed in patents CN100569753C, CN101337931B, CN101337932B and CN101337933B respectively. It can be known according to the test data in the patents that crystal forms A and C are more stable than crystal forms B and I.

The prior art WO2018164436 also discloses a crystal form M of mesylate, but the solubility thereof is still not evidently improved.

It is well known that, for the polymorphs of a medicament, different crystal forms can have different chemical and physical properties, including chemical stability, solubility, optical and mechanical properties, etc., which can directly affect the processing and production procedure of APIs and preparations, as well as the stability, solubility and bioavailability of the preparations. Therefore, the study on crystal forms is of great significance to the quality, safety and effectiveness of pharmaceutical preparations.

It is desired in the art to develop new crystal forms that are more suitable than the existing technology and can be used for industrialized mass production, while the invention meets such a requirement.

SUMMARY OF THE INVENTION

The invention unexpectedly discovers a new crystal form of lenvatinib mesylate with better solubility and better stability, which is named as crystal form X, through carrying out in-depth researches on lenvatinib mesylate. Lenvatinib mesylate is the mesylate of the compound of formula (I):

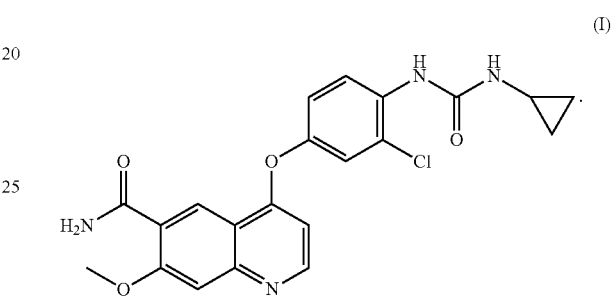

An X-ray powder diffraction spectrum of crystal form X of the mesylate provided by the invention has characteristic peaks at 2 theta values of 22.84°±0.2°, 20.16°±0.2°, and 9.46°±0.2°.

Further, the X-ray powder diffraction spectrum of crystal form X of the mesylate provided by the invention has characteristic peaks at 2 theta values of 22.84°±0.2°, 20.16°±0.2°, 9.46°±0.2°, 14.52°±0.2°, 24.86°±0.2° and 18.92°±0.2°.

Furthermore, the X-ray powder diffraction spectrum of crystal form X of the mesylate provided by the invention has characteristic peaks at 2 theta values of 22.84°±0.2°, 20.16°±0.2°, 9.46°±0.2°, 14.52°±0.2°, 24.86°±0.2°, 18.92°±0.2°, 26.82°±0.2°, 8.68°±0.2°, and 10.32°±0.2°.

More specifically, the invention provides an embodiment of crystal form X of the mesylate, performing X-ray powder measurement with Cu-Kα rays. Crystal form X has the diffraction angles, interplanar spacing and relative intensities shown in the following table:

| Peak No. | Pos. [°2Th.] | d-spacing [Å] | Rel. int. [%] |
|---|---|---|---|
| 1 | 8.68 | 10.179 | 30.5 |
| 2 | 9.46 | 9.338 | 45.6 |
| 3 | 10.32 | 8.563 | 21.9 |
| 4 | 14.60 | 6.064 | 41.2 |
| 5 | 17.54 | 5.053 | 34.1 |
| 6 | 18.92 | 4.687 | 57.8 |
| 7 | 20.16 | 4.400 | 79.0 |
| 8 | 20.74 | 4.280 | 29.5 |
| 9 | 21.56 | 4.119 | 28.6 |
| 10 | 22.24 | 3.994 | 50.6 |
| 11 | 22.84 | 3.890 | 100.0 |
| 12 | 23.32 | 3.811 | 32.5 |
| 13 | 23.82 | 3.732 | 41.5 |
| 14 | 24.86 | 3.579 | 38.6 |

-continued

| Peak No. | Pos. [°2Th.] | d-spacing [Å] | Rel. int. [%] |
|---|---|---|---|
| 15 | 25.44 | 3.499 | 26.6 |
| 16 | 26.82 | 3.321 | 43.8 | wherein, the error of the 2θ diffraction angle is ±0.2.

A DSC diagram of crystal form X of the mesylate provided by the invention has characteristic absorption peaks at 245.1° C. and 249.63° C.

Furthermore, crystal form X of the mesylate provided by the invention has an X-ray powder diffraction spectrum substantially as shown in FIG. 1 of the specification.

A differential scanning calorimetry diagram of crystal form X of lenvatinib mesylate provided by the invention is substantially as shown in FIG. 2 of the specification.

A thermogravimetric analysis diagram of crystal form X of lenvatinib mesylate provided by the invention is substantially as shown in FIG. 3 of the specification.

The invention also provides a preparation method for crystal form X of the mesylate of the compound of formula (I), specifically, adding the compound of formula (I) and methanesulfonic acid into an appropriate crystallization solvent, dissolving by heating, then cooling down and stirring to give the same.

Wherein, the crystallization solvent comprises one or more solvent systems of water and alcohols. The alcohol is preferably methanol.

The crystallization solvent can be a mixed system of water and alcohols, wherein the volume ratio of water to methanol is (9 mL~10 mL): 1 mL.

Specifically, the preparation method for crystal form X of the mesylate of the compound of formula (I) may comprise the following steps: suspending lenvatinib in a mixed solvent of methanol and water to obtain a suspension; adding methanesulfonic acid into the suspension dropwise, which is heated to be dissolved to clear, stirred at room temperature for crystallization, centrifuged to remove the lower solid; drying the solid to give the same. Furthermore, the mass-volume ratio of lenvatinib to the mixed solvent of methanol and water is preferably 1 g:(10 mL~11 mL), the volume ratio of methanol to water is preferably (9 mL~10 mL):1 mL, the dissolution temperature is preferably 60° C. to 70° C., and the crystallization time is preferably 20 hours or more. The drying is preferably performed at room temperature.

The invention provides use of crystal form X of the mesylate of the compound of formula (I) in the preparation of a medicament for treating cancer, in particular a pharmaceutical preparation for thyroid carcinoma and liver cancer.

Crystal form X of lenvatinib mesylate prepared by adopting the technical solution of the invention has the following advantages:
1. Compared with the existing crystal forms of lenvatinib mesylate, crystal form X of lenvatinib mesylate provided by the invention has significantly improved solubility.
2. When preparing crystal form X of lenvatinib mesylate by using the method of the invention, the reaction conditions are mild, the operation is simple, and the reproducibility is good. By using a single recrystallization method, the amount of solvent required is small, which is beneficial to recycling, can effectively cut the reagent cost and save energy, and is good for the environment protection.
3. By controlling the key process parameters of the preparation method of the invention, the yield and quality of lenvatinib mesylate can be significantly improved, with a high purity, good dissolution effect, and stable crystal form quality, enabling to achieve controllable industrial production conditions.

DESCRIPTION OF THE DRAWINGS

FIG. 7a1 is a comparative XRPD spectrum of the crystal form of lenvatinib mesylate in Example 2 placed for 7 days under a high humidity condition;

FIG. 7a2 is a comparative XRPD spectrum of the crystal form of lenvatinib mesylate in Example 2 placed for 1 month under a high humidity condition;

EMBODIMENTS OF THE INVENTION

The invention will be further described in detail below in conjunction with specific examples. The examples of the invention are only used to illustrate the technical solutions of the invention, and do not limit the essence and scope of the invention.

The explanations of the abbreviations used in the invention are as follows:
XRPD: X-ray powder diffraction
DSC: Differential Scanning Calorimetry
TGA: Thermogravimetric Analysis
$^1$H-NMR: Liquid nuclear magnetic hydrogen spectrum
$^{13}$C-NMR: Liquid nuclear magnetic carbon spectrum In the following examples, the test methods were generally implemented under conventional conditions or in accordance with conditions recommended by the manufacturer.

The structure of a compound was determined by nuclear magnetic resonance ($^1$H NMR). Nuclear magnetic resonance ($^1$H NMR) shift (δ) was given in the unit of parts per million (ppm); the measurement of nuclear magnetic resonance ($^1$H NMR) was carried out with Bruker AVANCE-400 nuclear magnetic instrument, with the solvent of hexadeuterated dimethyl sulfoxide ($CDCl_3$), and the internal standard of tetra methylsilane (TMS).

The X-ray powder diffraction spectrum (XRPD) of the invention was measured by using Liaoning Dandong Haoyuan DX-2700X powder diffractometer. The specific parameters were shown in the following table:

| X-ray diffraction parameter | Cu , Kα Kα1:1.540598 ; Kα2:1.544426 Kα2/Kα1 intensity ratio: 0.50 |
|---|---|

-continued

| | |
|---|---|
| Voltage | 40 kilovolt (kV) |
| Current | 30 milliampere (mA) |
| Scanning range (2θ°) | 3.0 to 40.0 degree |
| Bragg angle (2θ°) | 0.02 degree |

The differential scanning calorimetry (DSC) measurement data of the invention were collected on TAQ2000 differential scanning calorimeter, and the instrument parameters were shown in the following table:

| DSC | |
|---|---|
| Sample pan | Aluminum pan, gland |
| Temperature range | room temperature to 300° C. |
| Scanning rate | 10° C./min |
| Protective gas | Nitrogen |

The thermogravimetric analysis (TGA) measurement data of the invention were collected on TAQ5000 thermogravimetric analyzer, and the instrument parameters were shown in the following table:

| TGA | |
|---|---|
| Sample pan | Platinum pan, open |
| Temperature range | room temperature to 350° C. |
| Scanning rate | 10° C./min |
| Protective gas | Nitrogen |

"Room temperature" in the invention refers to a temperature between 10° C. and 25° C.

Figure 4:
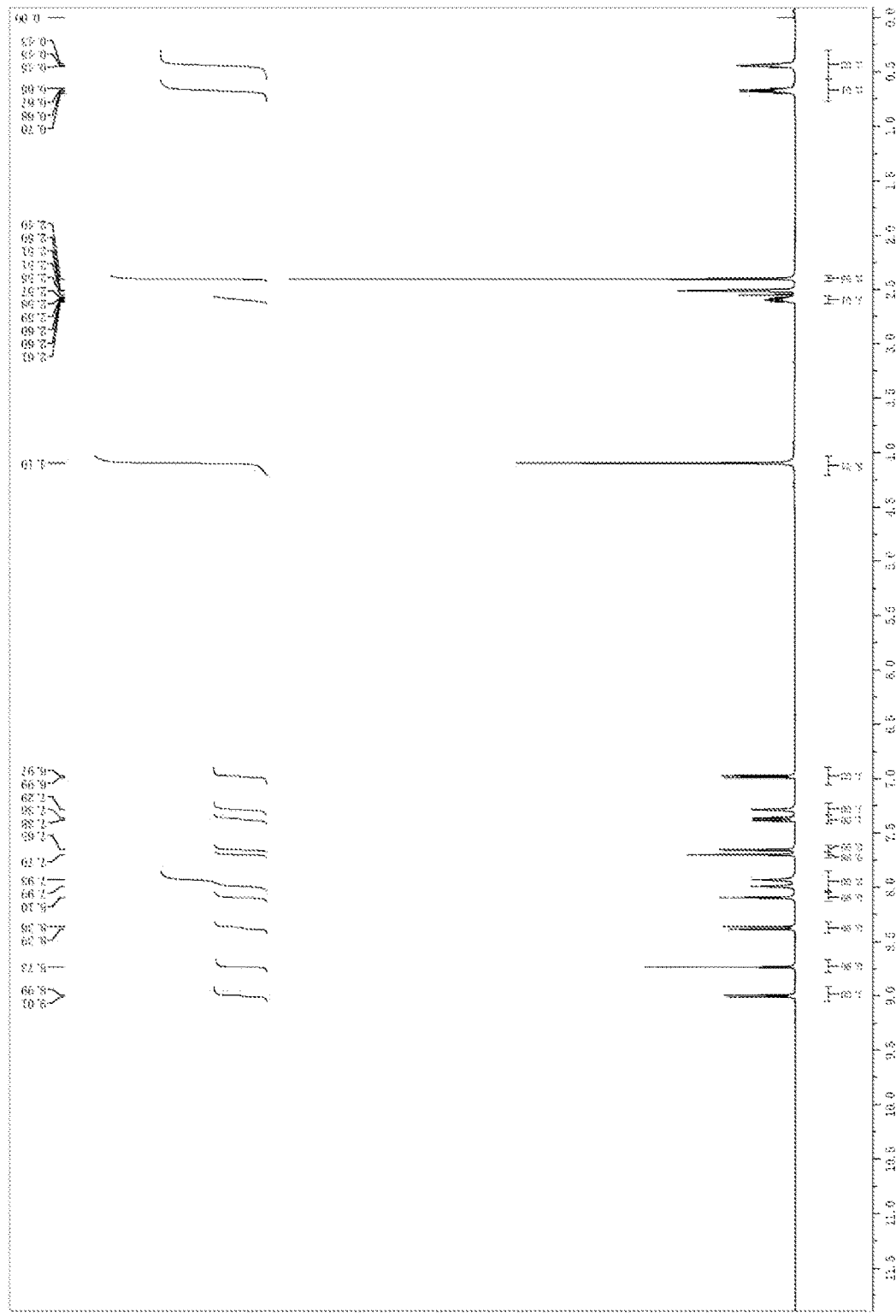
FIG. 4 is the $^1$H-NMR spectrum of crystal form X of lenvatinib mesylate.
Figure 5:
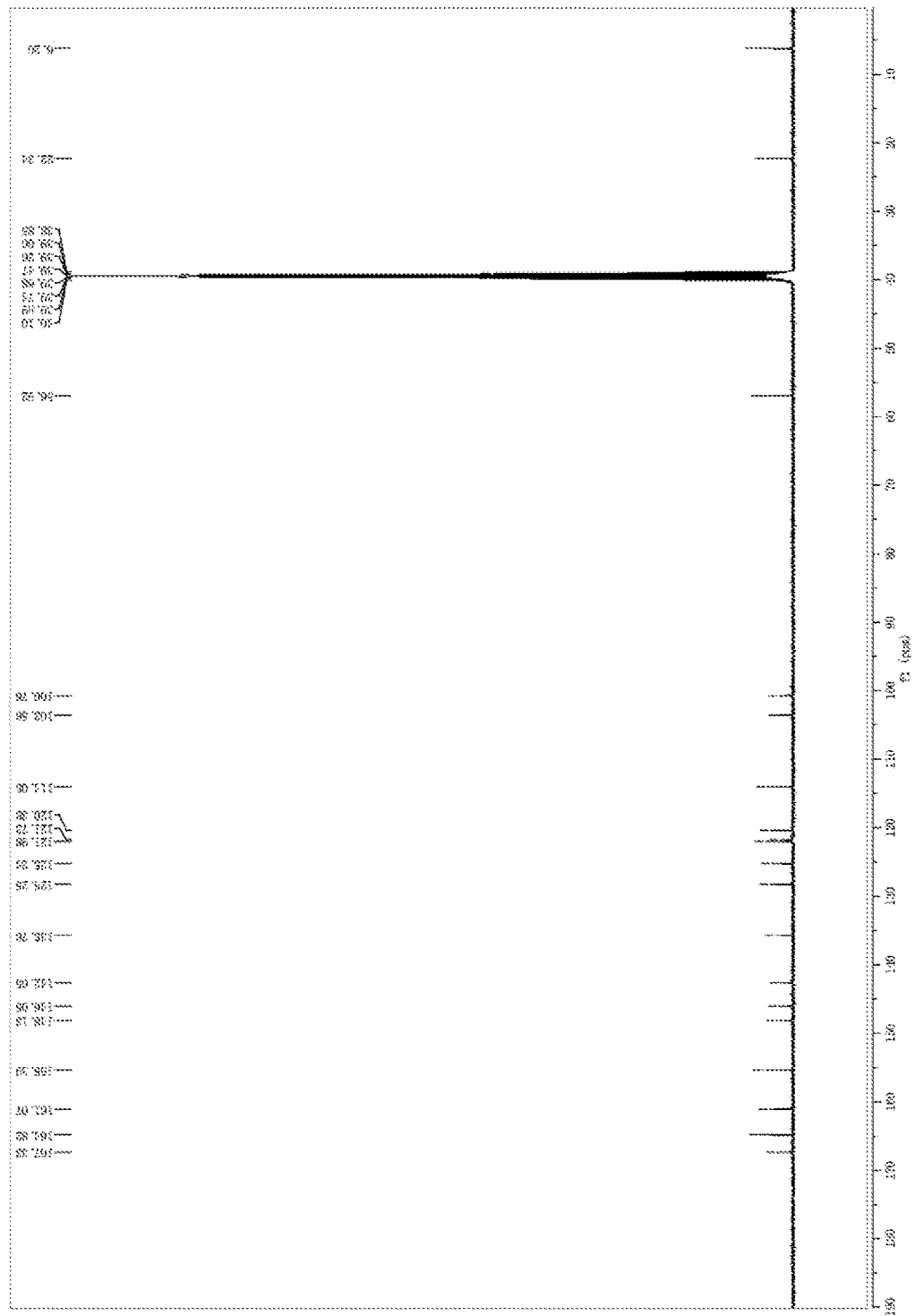
FIG. 5 is the $^{13}$C-NMR spectrum of crystal form X of lenvatinib mesylate.
Figure 6:
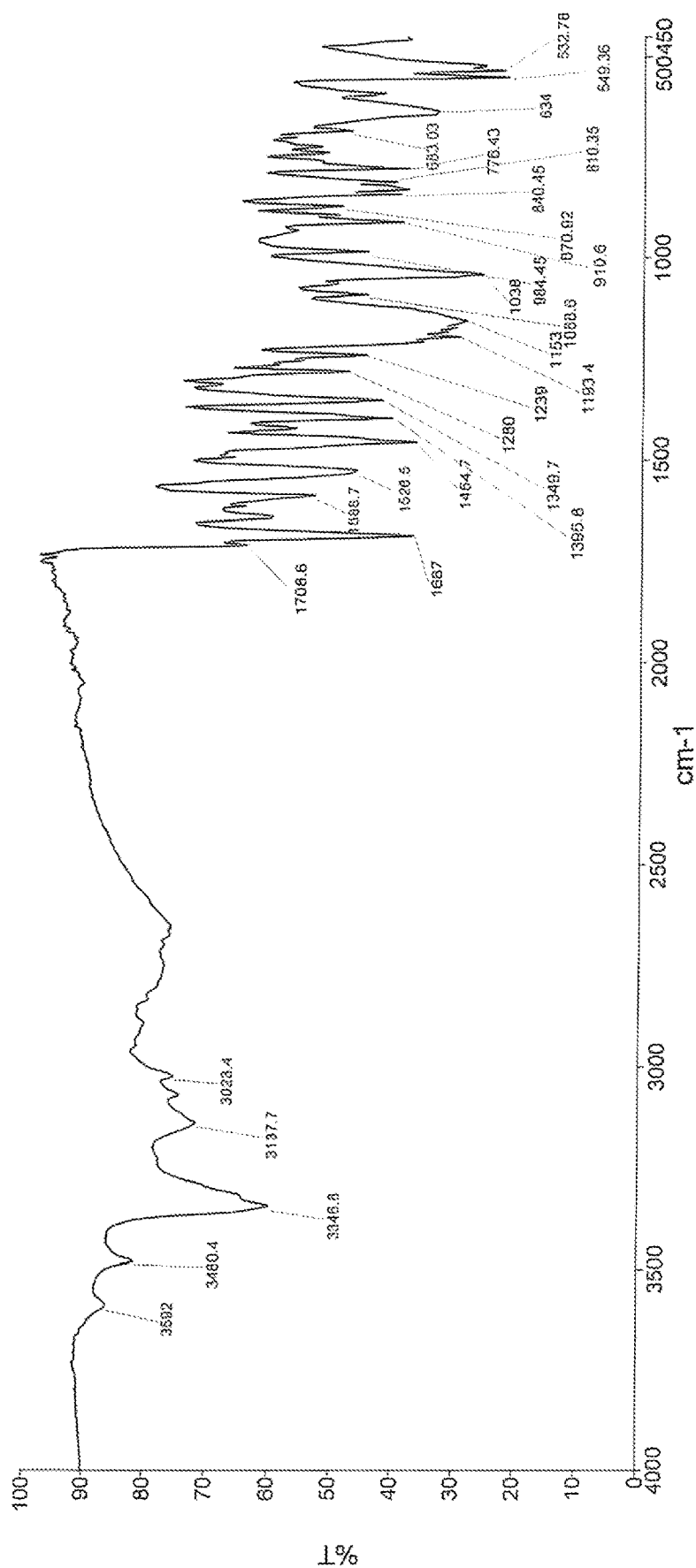
FIG. 6 is the infrared spectrum of crystal form X of lenvatinib mesylate.
Figure 7B:
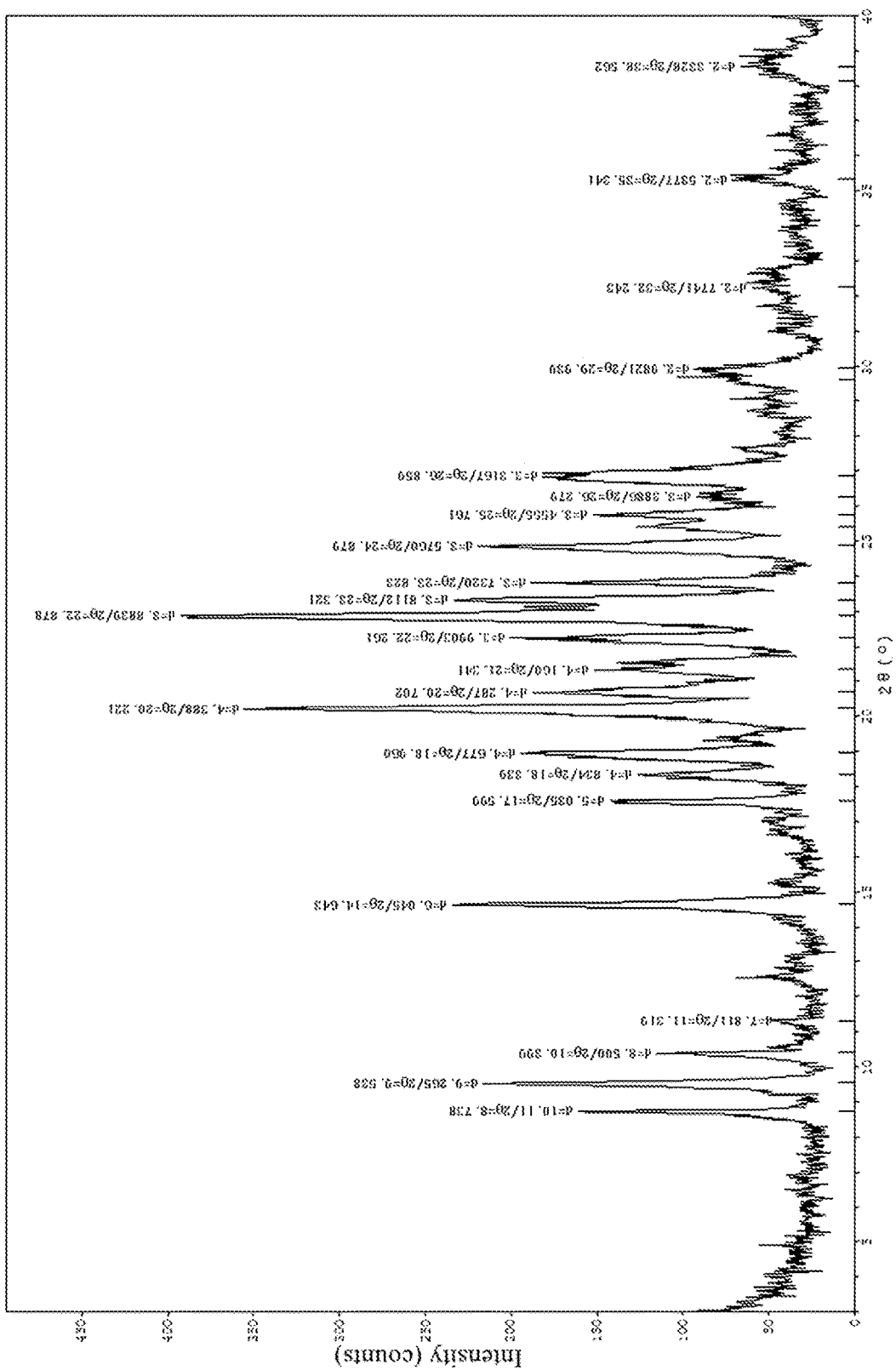
FIG. 7b is a comparative XRPD spectrum of the crystal form of lenvatinib mesylate in Example 2 placed for 10 days at 2° C. to 8° C.
Figure 7C:
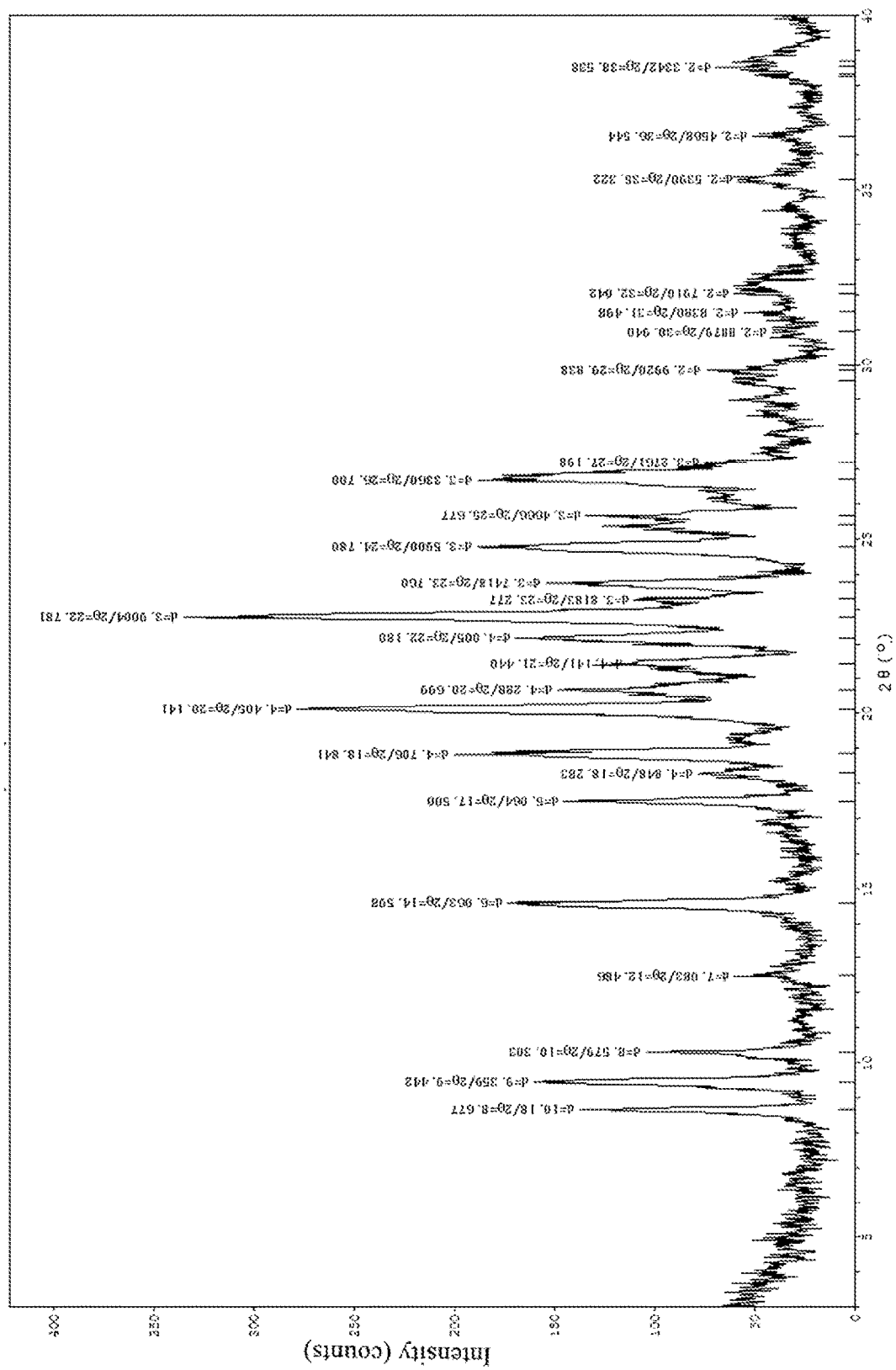
FIG. 7c is a comparative XRPD spectrum of the crystal form of lenvatinib mesylate in Example 2 placed for 7 days under a strong light condition.

Example 1: Preparation of Crystal Form X of Lenvatinib Mesylate 20 g of lenvatinib was suspended in a mixed solvent of 180 ml of methanol and 20 ml of water, 4.5 g of methanesulfonic acid (1.0 equivalent) was taken and slowly added to the suspension dropwise, which was stirred at room temperature for 30 minutes, and then heated to 55° C. to dissolve the solid completely. After the solid was completely dissolved, it was filtered while hot. The filtrate was naturally cooled down to room temperature, stirred at room temperature for 20 hours, centrifuged to remove the lower solid, and the obtained solid was dried overnight at a constant temperature of 25° C. The obtained solid was determined as crystal form X of lenvatinib mesylate, with the yield of 71%, and the purity thereof was detected by HPLC as 99.23%. The XRPD spectrum of crystal form X obtained in this example was shown in FIG. 1, $^1$H-NMR was shown in FIG. 4, $^{13}$C-NMR was shown in FIG. 5, and the infrared spectrum was shown in FIG. 6. Wherein, the diffraction angle, interplanar spacing and relative intensity of X-ray powder diffraction were shown in Table 1.

TABLE 1

| Peak No. | Pos. [°2Th.] | d-spacing [Å] | Rel. int. [%] |
|---|---|---|---|
| 1 | 8.68 | 10.179 | 30.5 |
| 2 | 9.46 | 9.338 | 45.6 |
| 3 | 10.32 | 8.563 | 21.9 |
| 4 | 14.58 | 6.064 | 41.2 |
| 5 | 17.54 | 5.053 | 34.1 |
| 6 | 18.92 | 4.687 | 57.8 |
| 7 | 20.16 | 4.400 | 79.0 |
| 8 | 20.74 | 4.280 | 29.5 |
| 9 | 21.56 | 4.119 | 28.6 |
| 10 | 22.24 | 3.994 | 50.6 |
| 11 | 22.84 | 3.890 | 100.0 |
| 12 | 23.32 | 3.811 | 32.5 |
| 13 | 23.82 | 3.732 | 41.5 |
| 14 | 24.86 | 3.579 | 38.6 |
| 15 | 25.44 | 3.499 | 26.6 |
| 16 | 26.82 | 3.321 | 43.8 |

The error of the 2θ diffraction angle was ±0.2.
$^1$H-NMR data were as follows:
$^1$H NMR (400 MHz, $d_6$-DMSO) δ 9.00 (d, J=6.6 Hz, 1H), 8.73 (s, 1H), 8.37 (d, J=9.1 Hz, 1H), 8.10 (s, 1H), 7.96 (d, J=24.3 Hz, 2H), 7.70 (s, 1H), 7.66 (d, J=2.8 Hz, 1H), 7.38 (dd, J=9.1, 2.8 Hz, 1H), 7.29 (d, J=2.4 Hz, 1H), 6.98 (d, J=6.6 Hz, 1H), 4.10 (s, 3H), 2.59 (m, 1H), 2.40 (s, 3H), 0.65-0.70 (m, 2H), 0.57-0.30 (m, 2H).
$^{13}$C-NMR data were as follows:
$^{13}$C NMR (101 MHz, $d_6$-DMSO) δ 167.33, 164.82, 161.07, 155.39, 148.13, 146.05, 142.65, 135.76, 128.25, 125.24, 121.98, 121.73, 120.38, 114.05, 103.56, 100.76, 56.92, 40.10, 39.89, 39.74, 39.68, 39.47, 39.26, 39.06, 38.85, 22.34, 6.20.

The infrared data were as follows:
Absorption peaks (cm$^{-1}$): 532.78, 549.36, 634, 683.03, 776.43, 810.35, 840.45, 870.92, 910.6, 984.45, 1038, 1088.6, 1153, 1193.4, 1239, 1280, 1349.7, 1395.8, 1454.7, 1526.5, 1588.7, 1687, 1708.6, 3023.4, 3137.7, 3345.8, 3480.4, 3592.

Figure 2:
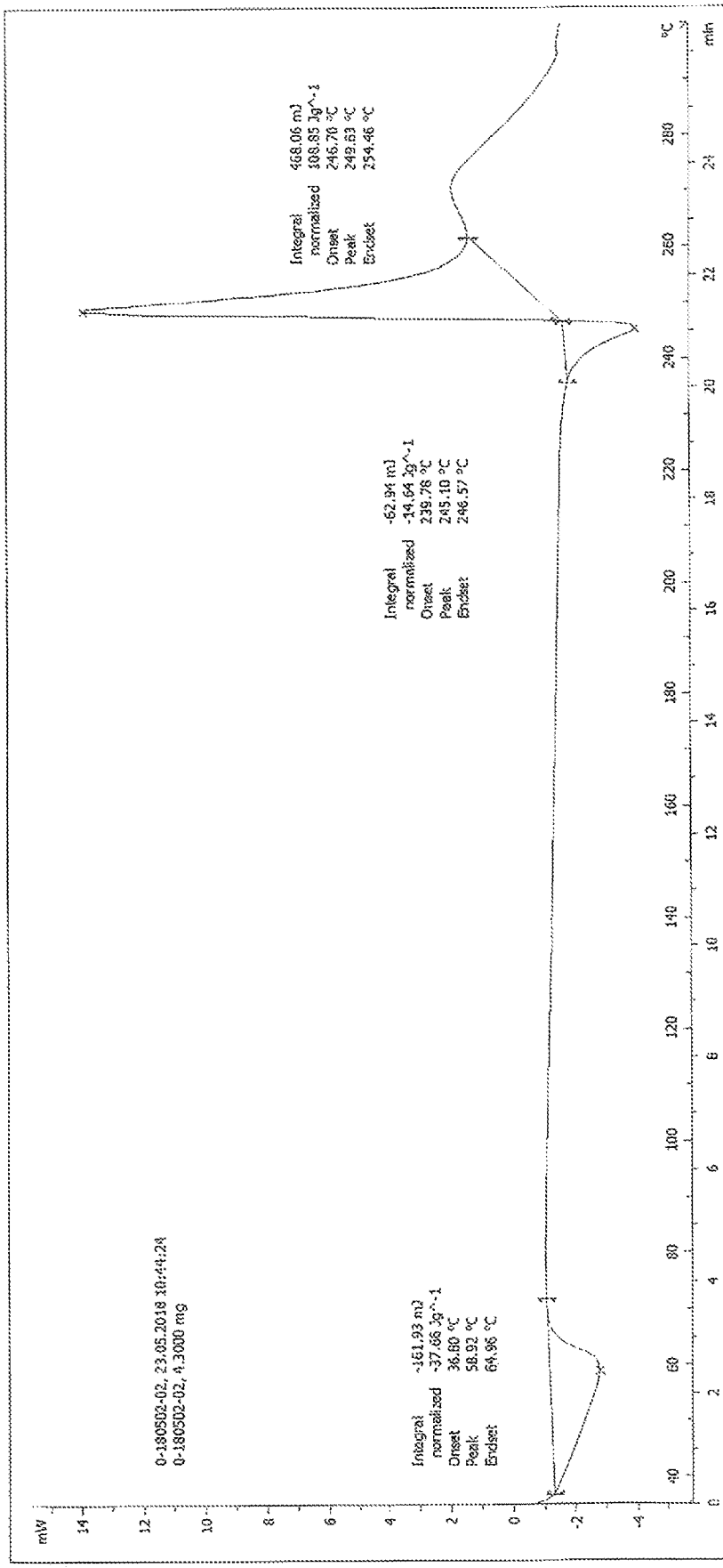
FIG. 2 is the DSC diagram of crystal form X of lenvatinib mesylate.
Figure 3:
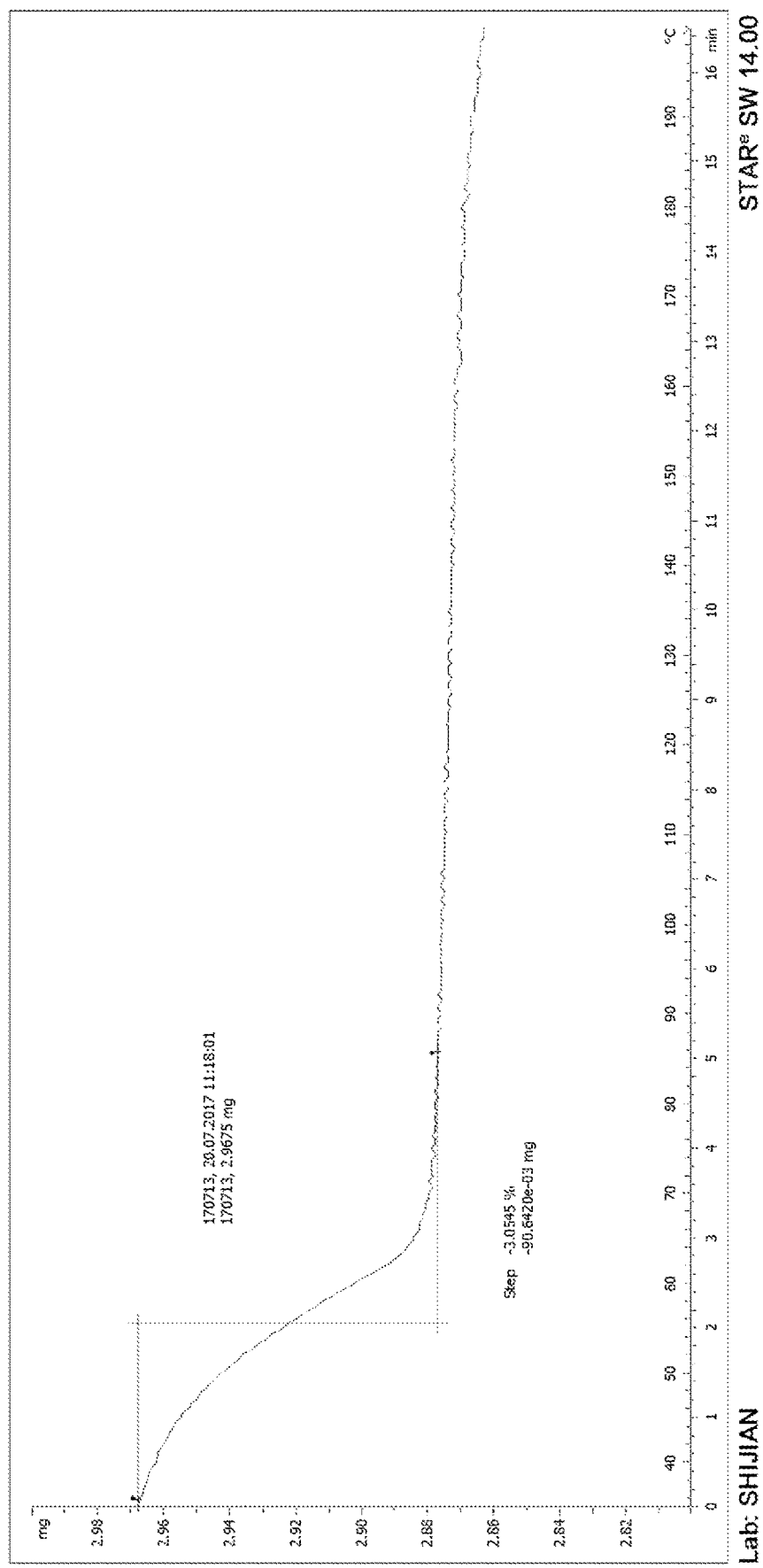
FIG. 3 is the TGA diagram of crystal form X of lenvatinib mesylate.

The DSC of crystal form X was as shown in FIG. 2 of the specification.
TGA was as shown in FIG. 3 of the specification.

Example 2: Preparation Method of Crystal Form X of Lenvatinib Mesylate 2.0 kg of lenvatinib was suspended in a mixed solvent of 18.0 L of methanol and 2.0 L of water, 0.45 kg of methanesulfonic acid (1.0 equivalent) was taken and slowly added to the suspension dropwise (adding dropwise for 2.5 hours), which was stirred at room temperature for 30 minutes, and then heated to 55° C. to dissolve the solid completely (dissolving for about 2.0 hours). After the solid was completely dissolved, it was filtered while hot. The filtrate was naturally cooled down to room temperature, stirred at room temperature for 20 hours, centrifuged to remove the lower solid, and the obtained solid was dried overnight at a constant temperature of 25° C. The obtained solid was determined as crystal form X of lenvatinib mesylate, with the yield of 78%, and the purity thereof was detected by HPLC as 99.14%.

The X-ray powder diffraction data of crystal form X obtained in this example were as shown in Table 2.

TABLE 2

| Peak No. | Pos. [°2Th.] | d-spacing [Å] | Rel. int. [%] |
|---|---|---|---|
| 1 | 8.66 | 10.205 | 27.5 |
| 2 | 9.48 | 9.325 | 46.9 |
| 3 | 10.28 | 8.595 | 19.0 |
| 4 | 14.54 | 6.086 | 44.5 |

TABLE 2-continued

| Peak No. | Pos. [°2Th.] | d-spacing [Å] | Rel. int. [%] |
|---|---|---|---|
| 5 | 17.52 | 5.059 | 23.7 |
| 6 | 18.82 | 4.711 | 38.8 |
| 7 | 20.20 | 4.393 | 66.3 |
| 8 | 20.70 | 4.288 | 22.6 | obtained in Example 2 and crystal form C were respectively added to 500 ml of medium with a pH of 1.0 (prepared with hydrochloric acid) and 500 ml of medium with a pH of 6.8 (prepared with potassium dihydrogen phosphate buffer solvent), stirred at 37° C. (50 r/min). At 5 min, 10 min, 15 min, 20 min, 30 min, 45 min and 60 min, the concentrations of lenvatinib in the medium were determined by using high performance liquid chromatography. The experimental results were shown in Table 3 below.

TABLE 3

| | Time (min) | 5 | 10 | 15 | 20 | 30 | 45 | 60 |
|---|---|---|---|---|---|---|---|---|
| pH 1.0 | Crystal form X (mg/ml) | 1.48 | 1.54 | 1.54 | 1.52 | 1.56 | 1.57 | 1.60 |
| | Crystal form C (mg/ml) | 0.41 | 0.47 | 0.52 | 0.55 | 0.61 | 0.67 | 0.72 |
| pH 6.8 | Crystal form X (mg/ml) | 0.0036 | 0.0038 | 0.0039 | 0.0039 | 0.0039 | 0.0039 | 0.0040 |
| | Crystal form C (mg/ml) | 0.0027 | 0.0030 | 0.0031 | 0.0032 | 0.0033 | 0.0034 | 0.0035 |

TABLE 2-continued

| Peak No. | Pos. [°2Th.] | d-spacing [Å] | Rel. int. [%] |
|---|---|---|---|
| 9 | 21.48 | 4.134 | 20.7 |
| 10 | 22.22 | 3.998 | 33.8 |
| 11 | 22.80 | 3.897 | 100.0 |
| 12 | 23.32 | 3.811 | 13.5 |
| 13 | 23.80 | 3.736 | 31.4 |
| 14 | 24.82 | 3.584 | 44.0 |
| 15 | 25.36 | 3.509 | 19.3 |
| 16 | 26.90 | 3.312 | 37.1 |

The error of the 2θ diffraction angle is ±0.2.

Figure 8:
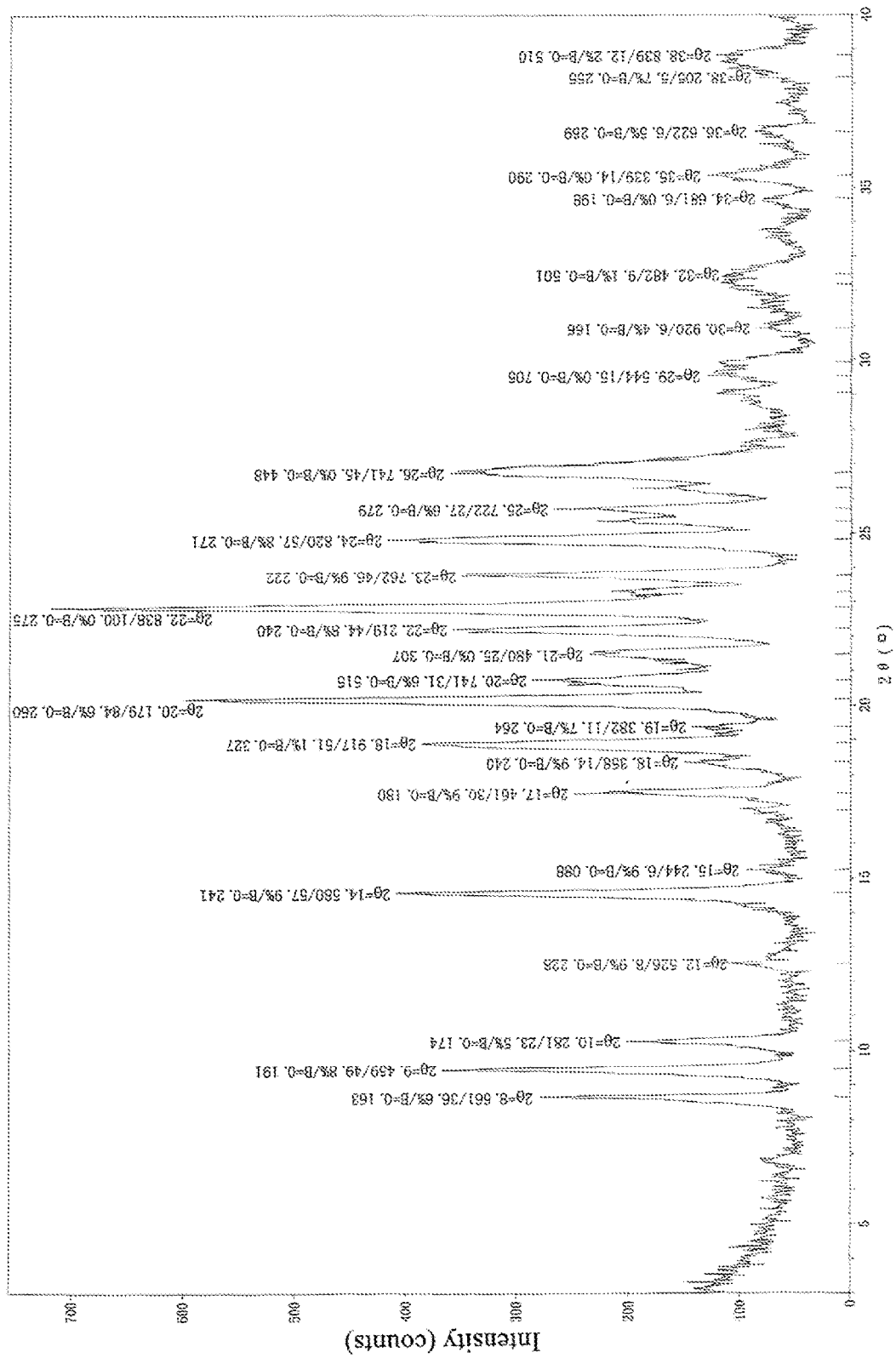
FIG. 8 is an XRPD spectrum of crystal form X of lenvatinib mesylate in Example 2 at day 0.

The powder diffraction data were substantially consistent with those in Example 1, as shown in FIG. 8.

Example 3: Preparation Method of Crystal Form X of Lenvatinib Mesylate 20.0 g of lenvatinib was suspended in a mixed solvent of 200 mL of methanol and 20 mL of water, 4.5 g of methanesulfonic acid (1.0 equivalent) was taken and slowly added to the suspension dropwise, which was stirred at room temperature for 30 minutes, and then heated to 55° C. to dissolve the solid completely. After the solid was completely dissolved, it was filtered while hot. The filtrate was naturally cooled down to room temperature, stirred at room temperature for 20 hours, centrifuged to remove the lower solid, and the obtained solid was dried overnight at a constant temperature of 25° C. The obtained solid was determined as crystal form X of lenvatinib mesylate, with the yield of 73%, and the purity thereof was detected by HPLC as 99.24%.

Figure 1:
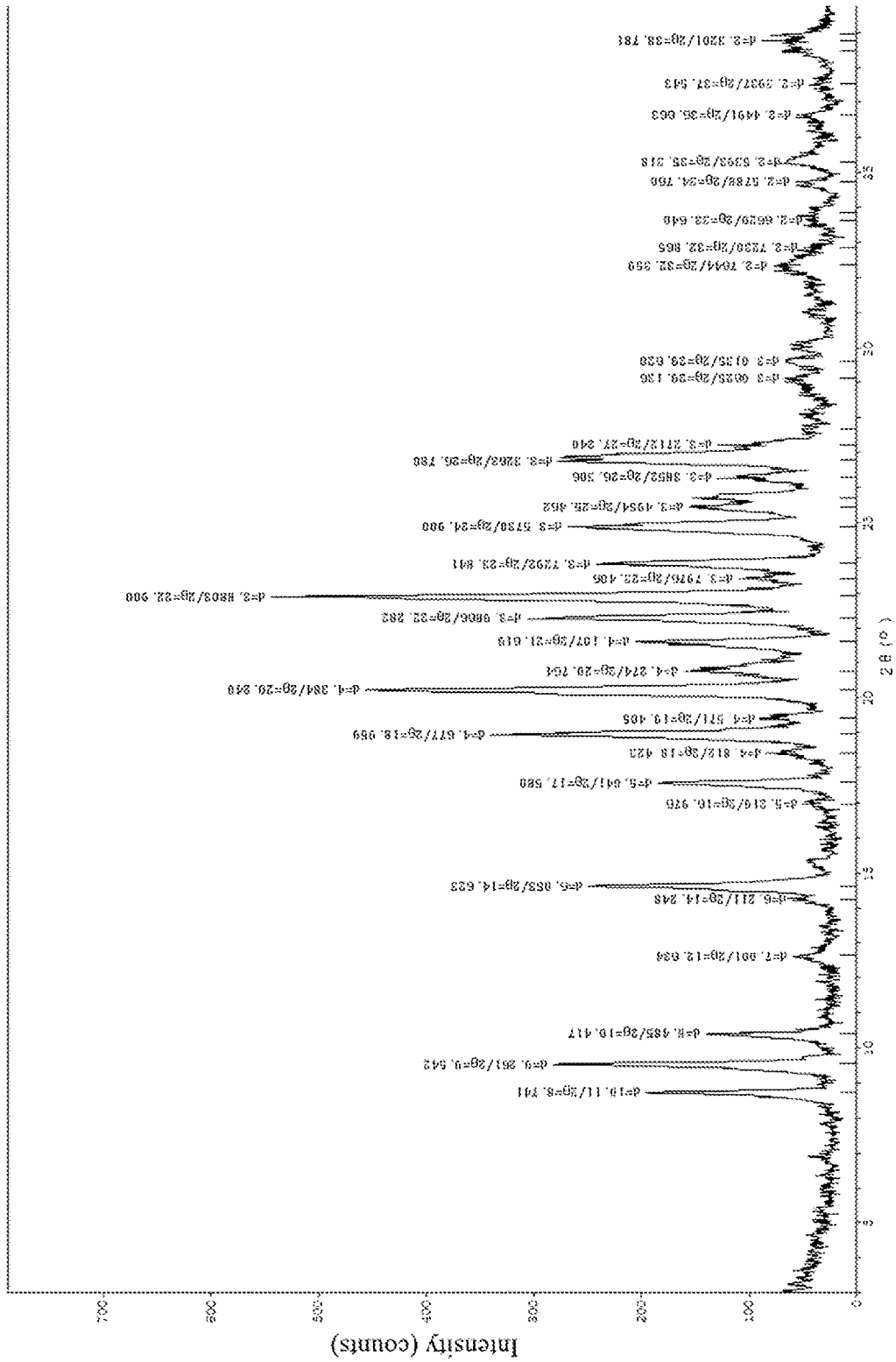
FIG. 1 is the XRPD spectrum of crystal form X of lenvatinib mesylate.

The X-ray powder diffraction data of crystal form X obtained in this example were substantially consistent with those in FIG. 1.

Test Example 1: Determination of the Dissolution Rate of Crystal Form X of Lenvatinib Mesylate In order to investigate the difference in the dissolution rate between the sample crystal form X in the examples of the invention and the anhydrous crystal form C disclosed in the patent CN100569753C, the samples of crystal form X The results of the dissolution rate test indicated that compared with crystal form C of lenvatinib mesylate, crystal form X of the invention showed an excellent dissolution rate and solubility, especially in a medium with a pH of 1.0, the dissolution rate within 5 minutes was 3 times higher than crystal form C.

Test Example 2: Stability Study of Crystal Form X of Lenvatinib Mesylate 6 samples of crystal form X of lenvatinib mesylate were taken, placed in the clean culture dishes and spread out while keeping open, respectively. a) The stabilities of the samples were investigated under a high humidity (25° C., RH 93.5%) condition, specimens were respectively taken at day 7 and day 30, and XRPD tests were performed on the specimens before and after the placement and compared; b) the stabilities of the samples after 10 days of the placement at a storage temperature of 2-8° C. were investigated, and XRPD tests were performed on the samples before and after the placement and compared; c) the stabilities of the samples after 7 days of the placement under the illumination of the strong light (1.2×10$^6$ Lux±500 Lx) were investigated, and XRPD tests were performed on the samples before and after the placement and compared. The results were shown in Table 4 below. It can be seen from the results in Table 4 that crystal form X of lenvatinib mesylate of the invention did not undergo crystal transformation before and after the stability tests, and the characteristic peaks maintained a high degree of consistency, demonstrating that crystal form X of lenvatinib mesylate of the invention has quite good stability.

TABLE 4

Results of the stability tests

| Condition | | | Result of crystal form X |
|---|---|---|---|
| Humidity | 93.5% | 7 days | No obvious change in crystal form |
| | | 1 month | No obvious change in crystal form |
| Temperature | 2~8° C. | 10 days | No obvious change in crystal form |
| illumination | | 7 days | No obvious change in crystal form |

Test Example 3: Pharmacokinetic Study on Crystal Form X of Lenvatinib Mesylate in Rats 1 Test Materials
1.1 Test Drug
Crystal form X of lenvatinib mesylate, prepared in Example 1, provided by the Synthesis Laboratory of Chengdu Easton Biopharmaceuticals Co., Ltd., yellow solid, batch number: 190301.
1.2 Test Reagent
Corn oil, provided by Yihai Kerry Food Marketing Co., Ltd., batch number GB19111.
1.3 Preparation of Test Samples
About 20 mg of the test drug was taken, added into 8 mL of vegetable oil and shaken well, to prepare a 2.5 mg/mL suspension.
1.4 Test Instruments
1 mL syringe, ethyl alcohol, cotton, 15 mL centrifuge tube, blood collection tube, EP tube, etc.
2 Test Animals
6 SD rats, all males, 200-220 g, provided by Chengdu Dashuo Biotechnology Co., Ltd.
3 Test Method
The rats were intragastrically administered with 10 mg/kg of the drug. Before administration and at 5 min, 15 min, 30 min, 1 h, 2 h, 4 h, 6 h, 8 h, 24 h after administration, 0.2 mL of jugular blood was taken and placed in EDTA-K2 anticoagulant tube, centrifuged for 10 min at 3000 r/min. The plasma was separated and frozen in the refrigerator at −80° C. After all blood collections were completed, the blood drug concentration in each blood sample was analyzed and determined autonomously, and the parameters of the test drugs (Tmax, time to maximum plasma concentration; Cmax, maximum plasma concentration; $AUC_{last}$) were calculated. Based on the obtained parameters, the average value and standard deviation were calculated, and the detailed results were shown in Table 5.

TABLE 5

| Results of the pharmacokinetic test | | | |
|---|---|---|---|
| Test result | Tmax (h) | Cmax (ng/mL) | $AUC_{last}$ (h * ng/mL) |
| Crystal form X | 1.17 ± 0.41 | 9866.67 ± 2565.49 | 90867.23 ± 19610.04 |

It can be seen from Table 5 that the time for crystal form X of the invention to reach the maximum plasma concentration was 1.17±0.41 h, the maximum plasma concentration thereof was 9866.672565.49 ng/mL, and the $AUC_{last}$ thereof was 90867.23±19610.04 h*ng/mL, demonstrating that crystal form X has better absorption in vivo in animals, which is beneficial to improve the bioavailability of the drug, thereby enhancing the therapeutic effect of the same.

Test Example 4: The Pharmacokinetic Study on Crystal Form X of Lenvatinib Mesylate in Beagle Dogs Crystal form X of lenvatinib mesylate (the crystal form obtained in Example 1) was pulverized in a mortar and filled into capsules. Beagle dogs were administered orally (n=4), and then orally administrated with 10 mL of water. The dosage was set to 3 mg/kg by the free form. The dogs were fasted one day before the administration, and started to eat at 8 h after the administration. Blood was collected from the vein before and after the administration, placed in an anti-coagulation tube, centrifuged to separate the plasma, and frozen in the refrigerator at −80° C. After all blood collections were completed, the blood drug concentration in each blood sample was analyzed and determined, and the parameters of each test substance (Tmax, time to maximum plasma concentration; Cmax, maximum plasma concentration; $AUC_{last}$, etc.) were calculated. Based on the obtained parameters, the average value and standard deviation thereof were calculated. It can be seen from the test results that crystal form X has a better absorption in vivo in animals, which is beneficial to improve the bioavailability of the drug, thereby enhancing the therapeutic effect of the same.

What is claimed is:

1. Crystal form X of a mesylate of a compound of formula (I), wherein an X-ray powder diffraction spectrum thereof has characteristic peaks at 2 theta values of 22.84°±0.2°, 20.16°±0.2°, 9.46°±0.2°, 14.52°±0.2°, 24.86°±0.2°, 18.92°±0.2°, 26.82°±0.2°, 8.68°±0.2°, 10.32°±0.2°:

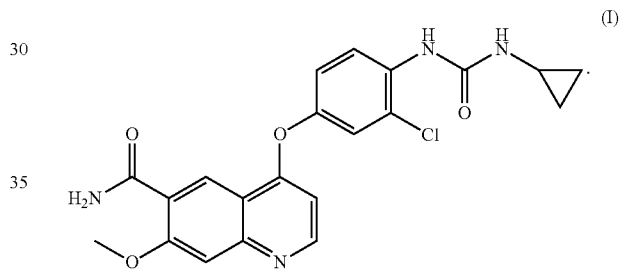

2. Crystal form X according to claim 1, wherein it has an X-ray powder diffraction spectrum as shown in FIG. 1.

3. Crystal form X according to claim 1, wherein a DSC diagram of the crystal form has characteristic absorption peaks at 245.1° C. and 249.63° C.

4. A preparation method for crystal form X of the mesylate of the compound of formula (I) according to claim 1, wherein the compound of formula (I) and methanesulfonic acid are added into an appropriate crystallization solvent which is a mixed system of water and methanol, and dissolved by heating, which is then cooled down and stirred to give the crystal form.

5. The preparation method according to claim 4, wherein the volume ratio of water to methanol is: 1 mL: (9 mL-10 mL).

6. A method for treating cancer in a subject in need thereof, comprising administering crystal form X of the mesylate of the compound of formula (I) according to claim 1 to the subject.

* * * * *